United States Patent
Geeganage

(10) Patent No.: US 8,334,293 B2
(45) Date of Patent: Dec. 18, 2012

(54) P70 S6 KINASE INHIBITOR AND EGFR INHIBITOR COMBINATION THERAPY

(75) Inventor: Sandaruwan Geeganage, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 13/126,484

(22) PCT Filed: Nov. 4, 2009

(86) PCT No.: PCT/US2009/063189
§ 371 (c)(1),
(2), (4) Date: Apr. 28, 2011

(87) PCT Pub. No.: WO2010/056575
PCT Pub. Date: May 20, 2010

(65) Prior Publication Data
US 2011/0207752 A1   Aug. 25, 2011

Related U.S. Application Data

(60) Provisional application No. 61/113,276, filed on Nov. 11, 2008.

(51) Int. Cl.
*A01N 43/90* (2006.01)
*A01N 43/50* (2006.01)
*A61K 31/519* (2006.01)
*A61K 31/415* (2006.01)
*C07D 239/70* (2006.01)

(52) U.S. Cl. ............... 514/262.1; 514/396; 544/253
(58) Field of Classification Search ............... 514/262.1, 514/396; 544/253
See application file for complete search history.

(56) References Cited

FOREIGN PATENT DOCUMENTS

| EP | 0817775 B1 | 9/2001 |
|---|---|---|
| WO | 2005/117909 A2 | 12/2005 |
| WO | 2006/046024 A1 | 5/2006 |
| WO | 2006/071819 A1 | 7/2006 |
| WO | 2007/047754 A2 | 4/2007 |
| WO | 2008/075109 A1 | 6/2008 |
| WO | 2008/140947 A1 | 11/2008 |

OTHER PUBLICATIONS

Melnikova et al. Nat. Reviews Drugs Discovery, 2004, vol. 3, pp. 993-994.*
Azzariti, et al. "Synergic antiproliferative and antiangiogenic effects of EGFR and mTor inhibitors on pancreatic cancer cells". Biochemical Pharmacology (2008) 75:1035-1044.
Dragowska, et al. "Decreased levels of hypoxic cells in gefitinib treated ER' HER-2 overexpressing MCF-7 breast cancer tumors are associated with hyperactivation of the mTOR pathway: therapeutic implications for combination therapy with rapamycin". Breast Cancer Res Treat (2007) 106:319-331.
Masiello, et al. "Combining an mTOR Antagonist and Receptor Tyrosine Kinase Inhibitors for the Treatment of Prostate Cancer". Cancer Biology and Therapy (2007) 6(2):195-201.

* cited by examiner

*Primary Examiner* — Samira Jean-Louis
(74) *Attorney, Agent, or Firm* — Tina M. Tucker

(57) ABSTRACT

The present invention provides a combination therapy comprising the compound 4-[4-[4-(4-fluoro-3-trifluoromethyl-phenyl)-1-methyl-1H-imidazol-2-yl]-piperidin-1-yl]-1H-pyrazolo[3,4-d]pyrimidine, or a pharmaceutically acceptable salt thereof, and an EGFR inhibitor for use in the treatment of glioblastoma multiforme, adenocarcinomas of the colon, non-small-cell lung cancer, small-cell lung cancer, cisplatin-resistant small-cell lung cancer, ovarian cancer, leukemia, pancreatic cancer, prostate cancer, mammary carcinoma, renal cell carcimoma, multiple myeloma, Kaposis Sarcoma, Hodgkins lymphoma, lymphangioleiomyomatosis, Non-Hodgkins lymphoma or sarcoma.

6 Claims, No Drawings

P70 S6 KINASE INHIBITOR AND EGFR INHIBITOR COMBINATION THERAPY

This application is a national phase application, under 35 U.S.C. 371, for PCT/US2009/063189 filed Nov. 4, 2009, which claims priority to U.S. Provisional Application No. 61/113,276 filed Nov. 11, 2008.

BACKGROUND OF THE INVENTION

The phosphotidylinositol-3-kinase (PI3K)/AKT/mammalian target of rapamycin (mTOR) pathway encompasses a number of signaling points which are critical in the control of cell growth and survival. P70 S6 kinase is a serine-threonine protein kinase which is a downstream effector of the PI3K/AKT/mTOR signaling pathway. P70 S6 kinase phosphorylates the ribosomal protein S6 in cells and regulates ribosome biogenesis, cell growth and cell cycle progression in response to mitogenic stimulation. P70 S6 kinase is commonly activated in many solid tumors. Inhibitors of p70 S6 kinase, which are useful in the treatment of such tumors, are disclosed in WO 2006/046024 and WO 2008/075109.

Epidermal growth factor receptor (EGFR) is a trans-membrane glycoprotein which belongs to a family of structurally related receptor tyrosine kinases. EGFR feeds into the PI3K/AKT/mTOR pathway at the cell surface level. EGFR is believed to be important in multiple signal-transduction pathways and appears to play a critical role in both tumorigenesis and tumor growth. EGFR and its ligands are overexpressed or involved in autocrine growth loops in a number of tumor types. EP 0 817 775 discloses a series of 4-(substitutedphenylamino)quinazoline derivatives which have EGFR inhibitory activity and are useful in the treatment of cancer.

There exists a need for improved therapies for the treatment of cancers. Furthermore, there is a need for therapies having greater efficacy than existing therapies. Preferred combination therapies of the present invention show greater efficacy than treatment with either therapeutic agent alone. More preferred combination therapies of the present invention show greater efficacy when sub-optimal doses of each of the therapeutic agents are administered.

BRIEF SUMMARY OF THE INVENTION

The present invention provides a product containing the compound 4-[4-[4-(4-fluoro-3-trifluoromethyl-phenyl)-1-methyl-1H-imidazol-2-yl]-piperidin-1-yl]-1H-pyrazolo[3,4-d]pyrimidine, or a pharmaceutically acceptable salt thereof, and an EGFR inhibitor as a combined preparation for simultaneous, separate or sequential use in therapy.

The present invention further provides a product containing the compound 4-[4-[4-(4-fluoro-3-trifluoromethyl-phenyl)-1-methyl-1H-imidazol-2-yl]-piperidin-1-yl]-1H-pyrazolo[3,4-d]pyrimidine, or a pharmaceutically acceptable salt thereof, and an EGFR inhibitor as a combined preparation for simultaneous, separate or sequential use in the treatment of glioblastoma multiforme, adenocarcinomas of the colon, non-small-cell lung cancer, small-cell lung cancer, cisplatin-resistant small-cell lung cancer, ovarian cancer, leukemia, pancreatic cancer, prostate cancer, mammary carcinoma, renal cell carcimoma, multiple myeloma, Kaposi's Sarcoma, Hodgkin's lymphoma, lymphangioleiomyomatosis, Non-Hodgkin's lymphoma or sarcoma.

The present invention further provides the compound 4-[4-[4-(4-fluoro-3-trifluoromethyl-phenyl)-1-methyl-1H-imidazol-2-yl]-piperidin-1-yl]-1H-pyrazolo[3,4-d]pyrimidine, or a pharmaceutically acceptable salt thereof, for use in simultaneous, separate or sequential combination with an EGFR inhibitor in the treatment of glioblastoma multiforme, adenocarcinomas of the colon, non-small-cell lung cancer, small-cell lung cancer, cisplatin-resistant small-cell lung cancer, ovarian cancer, leukemia, pancreatic cancer, prostate cancer, mammary carcinoma, renal cell carcimoma, multiple myeloma, Kaposi's Sarcoma, Hodgkin's lymphoma, lymphangioleiomyomatosis, Non-Hodgkin's lymphoma or sarcoma.

The present invention further provides a method of treating a cancer selected from the group consisting of glioblastoma multiforme, adenocarcinomas of the colon, non-small-cell lung cancer, small-cell lung cancer, cisplatin-resistant small-cell lung cancer, ovarian cancer, leukemia, pancreatic cancer, prostate cancer, mammary carcinoma, renal cell carcimoma, multiple myeloma, Kaposi's Sarcoma, Hodgkin's lymphoma, lymphangioleiomyomatosis, Non-Hodgkin's lymphoma and sarcoma comprising administering to a patient in need thereof the compound 4-[4-[4-(4-fluoro-3-trifluoromethyl-phenyl)-1-methyl-1H-imidazol-2-yl]-piperidin-1-yl]-1H-pyrazolo[3,4-d]pyrimidine, or a pharmaceutically acceptable salt thereof, and an EGFR inhibitor in amounts that in combination are effective.

DETAILED DESCRIPTION OF THE INVENTION

The compound 4-[4-[4-(4-fluoro-3-trifluoromethyl-phenyl)-1-methyl-1H-imidazol-2-yl]-piperidin-1-yl]-1H-pyrazolo[3,4-d]pyrimidine:

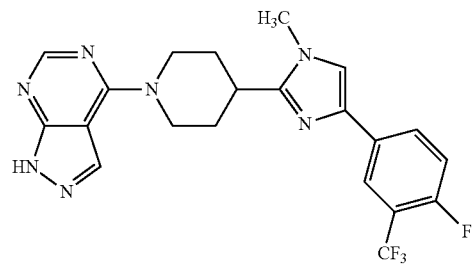

is a p70 S6 kinase inhibitor.

The compound 4-[4-[4-(4-fluoro-3-trifluoromethyl-phenyl)-1-methyl-1H-imidazol-2-yl]-piperidin-1-yl]-1H-pyrazolo[3,4-d]pyrimidine is a base, and accordingly will react with any of a number of organic and inorganic acids to form pharmaceutically acceptable salts. The term "pharmaceutically acceptable salt" as used herein, refers to salts of the compound 4-[4-[4-(4-fluoro-3-trifluoromethyl-phenyl)-1-methyl-1H-imidazol-2-yl]-piperidin-1-yl]-1H-pyrazolo[3,4-d]pyrimidine which are substantially non-toxic to living organisms. Such salts include the pharmaceutically acceptable salts listed in Journal of Pharmaceutical Science, 66, 2-19 (1977), which are known to the skilled artisan. The tosylate (also known as p-toluene sulfonate) and hydrochloride salts are preferred. The tosylate salt is especially preferred.

"EGFR Inhibitor" means any compound, peptide or antibody which is an inhibitor of EGFR. Preferred EGFR inhibitors include erlotinib, cetuximab (Erbitux®; disclosed in EP 0 359 282), panitumumab (Vectibix®; disclosed in EP 0 359 282) and gefinitib (Iressa®; disclosed in EP 0 566 226). A particularly preferred EGFR inhibitor is erlotinib, N-(3-ethynylphenyl)-6,7-bis-(2-methoxyethoxy)-4-quinazolinamine, and, in particular, erlotinib hydrochloride (Tarceva®). The EGFR inhibitor erlotinib and methods for its preparation are disclosed in EP 0 817 775.

The term "combination therapy" refers to treatment comprising the administration of the compound 4-[4-[4-(4-fluoro-3-trifluoromethyl-phenyl)-1-methyl-1H-imidazol-2-yl]-piperidin-1-yl]-1H-pyrazolo[3,4-d]pyrimidine, or a pharmaceutically acceptable salt thereof, and an EGFR inhibitor (the "therapeutic agents") in combination. The therapeutic agents may be administered simultaneously, separately or sequentially.

The term "treating" or "treatment" includes the slowing, interrupting, arresting, controlling, stopping, reducing, or reversing the progression or severity of a symptom, disorder, condition or disease.

The term "amounts that are in combination effective" means the amount of the compound 4-[4-[4-(4-fluoro-3-trifluoromethyl-phenyl)-1-methyl-1H-imidazol-2-yl]-piperidin-1-yl]-1H-pyrazolo[3,4-d]pyrimidine, or a pharmaceutically acceptable salt thereof, and the amount of the EGFR inhibitor which are effective in treating the disorders described herein when administered in combination. The amount of each therapeutic agent which is effective in combination may be equal to the amount which is effective when the therapeutic agent is administered on its own or it may be less than the amount which is effective when the therapeutic agent is administered on its own (i.e. it may be a sub-optimal dose).

The combination therapy described herein may be used in the treatment of proliferative disorders such as cancer and in the inhibition of angiogenesis in mammals. In all embodiments of the present invention, it is preferred that the cancer to be treated is selected from glioblastoma multiforme, adenocarcinomas of the colon, non-small-cell lung cancer, small-cell lung cancer, cisplatin-resistant small-cell lung cancer, ovarian cancer, leukemia, pancreatic cancer, prostate cancer, mammary carcinoma, renal cell carcimoma, multiple myeloma, Kaposi's Sarcoma, Hodgkin's lymphoma, lymphangioleiomyomatosis, Non-Hodgkin's lymphoma and sarcoma. It is especially preferred that the cancer to be treated is non-small-cell lung cancer. It is preferred that the mammal to be treated is a human.

In an alternative embodiment of the present invention, an EGFR inhibitor can be used in simultaneous, separate or sequential combination with the compound 4-[4-[4-(4-fluoro-3-trifluoromethyl-phenyl)-1-methyl-1H-imidazol-2-yl]-piperidin-1-yl]-1H-pyrazolo[3,4-d]pyrimidine, or a pharmaceutically acceptable salt thereof, in the treatment of cancer, in particular, the cancers described above.

The compound 4-[4-[4-(4-fluoro-3-trifluoromethyl-phenyl)-1-methyl-1H-imidazol-2-yl]-piperidin-1-yl]-1H-pyrazolo[3,4-d]pyrimidine, or a pharmaceutically acceptable salt thereof, can be used in the manufacture of a medicament for use in combination therapy for treating cancer, in particular, the cancers described above, wherein said medicament is to be administered in combination with an EGFR inhibitor.

In a further alternative embodiment of the present invention, an EGFR inhibitor can be used in the manufacture of a medicament for use in combination therapy for treating cancer, in particular, the cancers described above, wherein said medicament is to be administered in combination with the compound 4-[4-[4-(4-fluoro-3-trifluoromethyl-phenyl)-1-methyl-1H-imidazol-2-yl]-piperidin-1-yl]-1H-pyrazolo[3,4-d]pyrimidine, or a pharmaceutically acceptable salt thereof.

In a further alternative embodiment, there is provided a pharmaceutical formulation comprising the compound 4-[4-[4-(4-fluoro-3-trifluoromethyl-phenyl)-1-methyl-1H-imidazol-2-yl]-piperidin-1-yl]-1H-pyrazolo[3,4-d]pyrimidine, or a pharmaceutically acceptable salt thereof, and an EGFR inhibitor, in combination with a pharmaceutically acceptable carrier, diluent, or excipient.

The compound 4-[4-[4-(4-fluoro-3-trifluoromethyl-phenyl)-1-methyl-1H-imidazol-2-yl]-piperidin-1-yl]-1H-pyrazolo[3,4-d]pyrimidine, or a pharmaceutically acceptable salt thereof, and the EGFR inhibitor can be administered by a variety of routes. They may be administered by the same route or by different routes. Preferably, the compound 4-[4-[4-(4-fluoro-3-trifluoromethyl-phenyl)-1-methyl-1H-imidazol-2-yl]-piperidin-1-yl]-1H-pyrazolo[3,4-d]pyrimidine, or a pharmaceutically acceptable salt thereof, or the EGFR inhibitor are administered orally. More preferably, both are administered orally.

The optimum dosage regimens for each of the therapeutic agents used in the combination therapy of the present invention may vary depending on, for example, the route of administration, the disease being treated and the EGFR inhibitor used. For example, the dose of the compound 4-[4-[4-(4-fluoro-3-trifluoromethyl-phenyl)-1-methyl-1H-imidazol-2-yl]-piperidin-1-yl]-1H-pyrazolo[3,4-d]pyrimidine, or a pharmaceutically acceptable salt thereof, may be in the range 100 mg to 2000 mg per day. Preferred doses are in the range 600 mg to 1600 mg per day. In a preferred embodiment, the compound is administered twice daily and each dose is in the range 300 mg to 800 mg. The dose of the EGFR inhibitor erlotinib hydrochloride may be in the range 10 mg to 450 mg per day. Preferred doses of erlotinib hydrochloride are 150 mg or 100 mg per day.

The combination therapy may be administered for a single fixed period of time, for example, 6 months. The combination therapy may be administered according to a cyclical schedule, where there are alternating treatment and non-treatment periods. Alternatively, the combination therapy may be administered continuously. It is preferred that the combination therapy is administered continuously (until disease progression or unacceptable toxicity).

In one embodiment, the compound 4-[4-[4-(4-fluoro-3-trifluoromethyl-phenyl)-1-methyl-1H-imidazol-2-yl]-piperidin-1-yl]-1H-pyrazolo[3,4-d]pyrimidine, or a pharmaceutically acceptable salt thereof, and the EGFR inhibitor are administered separately. When administered separately, the compound 4-[4-[4-(4-fluoro-3-trifluoromethyl-phenyl)-1-methyl-1H-imidazol-2-yl]-piperidin-1-yl]-1H-pyrazolo[3,4-d]pyrimidine, or a pharmaceutically acceptable salt thereof, and the EGFR inhibitor may be administered according to different dosing regimens and by different routes of administration.

In another embodiment, the compound 4-[4-[4-(4-fluoro-3-trifluoromethyl-phenyl)-1-methyl-1H-imidazol-2-yl]-piperidin-1-yl]-1H-pyrazolo[3,4-d]pyrimidine, or a pharmaceutically acceptable salt thereof, and the EGFR inhibitor are administered sequentially. In this embodiment either therapeutic agent may be administered first. Preferably, the EGFR inhibitor is administered first followed by the compound 4-[4-[4-(4-fluoro-3-trifluoromethyl-phenyl)-1-methyl-1H-imidazol-2-yl]-piperidin-1-yl]-1H-pyrazolo[3,4-d]pyrimidine, or a pharmaceutically acceptable salt thereof. It is preferred that the time between a dose of one therapeutic agent and a dose of the other is less than 8 hours. More preferably, less than 4 hours and even more preferably, less than 1 hour.

In yet another embodiment, the compound 4-[4-[4-(4-fluoro-3-trifluoromethyl-phenyl)-1-methyl-1H-imidazol-2-yl]-piperidin-1-yl]-1H-pyrazolo[3,4-d]pyrimidine, or a pharmaceutically acceptable salt thereof, and the EGFR inhibitor are administered simultaneously. In this embodiment, the agents may be administered in the same formulation or simultaneously via different routes of administration.

The therapeutic agent 4-[4-[4-(4-fluoro-3-trifluoromethyl-phenyl)-1-methyl-1H-imidazol-2-yl]-piperidin-1-yl]-1H-pyrazolo[3,4-d]pyrimidine tosylate is preferably administered orally. It is further preferred that two doses of 4-[4-[4-(4-fluoro-3-trifluoromethyl-phenyl)-1-methyl-1H-imidazol-2-yl]-piperidin-1-yl]-1H-pyrazolo[3,4-d]pyrimidine tosylate are administered per day over the course of the treatment and that each dose is in the range 300 mg to 800 mg.

In one embodiment, the therapeutic agents used in the combination therapy are 4-[4-[4-(4-fluoro-3-trifluoromethyl-phenyl)-1-methyl-1H-imidazol-2-yl]-piperidin-1-yl]-1H-pyrazolo[3,4-d]pyrimidine tosylate and erlotinib hydrochloride. It is preferred that 4-[4-[4-(4-fluoro-3-trifluoromethyl-phenyl)-1-methyl-1H-imidazol-2-yl]-piperidin-1-yl]-1H-pyrazolo[3,4-d]pyrimidine tosylate is administered orally according to the preferred dosing schedule described above. In this embodiment, it is preferred that erlotinib hydrochloride is also administered orally. It is further preferred that one dose of erlotinib is administered per day and that each dose is 100 mg or 150 mg. In this embodiment, it is preferred that the combination therapy is administered continuously.

The compound 4-[4-[4-(4-fluoro-3-trifluoromethyl-phenyl)-1-methyl-1H-imidazol-2-yl]-piperidin-1-yl]-1H-pyrazolo[3,4-d]pyrimidine, and pharmaceutically acceptable salts thereof, may be prepared according to the methods described below.

Preparation of the Intermediate
4-Chloro-1H-pyrazolo[3,4-d]pyrimidine

To a solution of allopurinol (20 g; 146.94 mmoles) in toluene (205.71 mL), add phosphoryl chloride (68.27 mL; 734.68 mmoles) and diisopropylethylamine (56.38 mL; 323.26 mmoles) and heat the mixture at 80° C. for 2 hours. Remove the solvent in vacuo to half and pour the mixture into 2 M potassium phosphate, dibasic (734.68 mL; 1.47 moles) in water at 4° C. Stir the mixture overnight at room temperature (RT). Filter off the precipitate through a pad of Celite® and wash it subsequently with EtOAc. Separate the filtrate, wash the aqueous layer with more EtOAc, join the organic layers, dry it over MgSO$_4$, filter and concentrate in vacuo to afford the title compound (16 g; 70.45% yield) as a yellow solid. MS (APCI): m/z=155.1 [M+H].

Preparation of 4-[4-[4-(4-Fluoro-3-trifluoromethyl-phenyl)-1-methyl-1H-imidazol-2-yl]-piperidin-1-yl]-1H-pyrazolo[3,4-d]pyrimidine hydrochloride Add methenamine (1.10 equiv; 231.55 mmoles; 32.46 g) to a solution of 4-fluoro-3-(trifluoromethyl)phenacyl bromide (60.00 g; 1.00 equiv; 210.50 mmoles) in ethyl acetate (450 mL; 4.60 moles). Stir the mixture at RT overnight. Remove the solvent in vacuo and triturate the solid in methyl tert-butyl ether (MTBE). Filter and dry under reduced pressure. Add ethanol (450 mL; 7.73 moles), followed by hydrogen chloride (150 mL; 8.30 equiv; 1.75 moles) and stir the mixture at RT overnight. Remove the solvent in vacuo and dry the solid in vacuo at 50° C. for a week to obtain 2-Amino-1-(4-fluoro-3-trifluoromethyl-phenyl)-ethanone hydrochloride (54.23 g; 100% yield) as a white solid.

Add N-methylmorpholine (3 equiv; 631.52 mmoles; 69.66 mL) to a solution of piperidine-1,4-dicarboxylic acid mono-tert-butyl ester (1.20 equiv; 252.61 mmoles; 57.92 g) in tetrahydrofuran (THF) (400 mL). Cool the mixture to −10° C. with a dry ice-acetone bath. Add isobutyl chloroformate (1.1 equiv; 231.56 mmoles; 30.26 mL) dropwise while maintaining the temperature below −5° C. After 30 min at −5°-10° C., add 2-amino-1-(4-fluoro-3-trifluoromethyl-phenyl)-ethanone hydrochloride (54.23 g; 1.00 equiv; 210.51 mmoles) suspended in THF (300 mL) and stir the mixture in the bath at −5° C. for 20 min. Stir for 1 hour at RT. Add water and EtOAc, then wash the organic layer with water and saturated aqueous sodium chloride. Dry over MgSO$_4$, filter and remove solvent in vacuo. Suspend the crude in MTBE and stir for 2 hours. Filter the solid and dry in vacuo to give 1-[2-(4-Fluoro-3-trifluoromethyl-phenyl)-2-oxo-ethylcarbamoyl]-piperidine-4-carboxylic acid tert-butyl ester (64.44 g; 70.79% yield).

Add ammonium acetate (15 equiv; 1.02 moles; 78.61 g) to a solution of 1-[2-(4-fluoro-3-trifluoromethyl-phenyl)-2-oxo-ethylcarbamoyl]-piperidine-4-carboxylic acid tert-butyl ester (29.4 g; 1.00 equiv; 67.99 mmoles) in 1-butanol (150 mL; 1.64 moles), then add triethylamine (1 equiv; 67.99 mmoles; 9.48 mL). Stir the mixture at 160° C. in a sealed tube for 3 h. Add EtOAc and water, then wash the organic layer with more water and saturated aqueous sodium chloride and concentrated in vacuo. Triturate the crude in MTBE, filter and dry under reduced pressure to give 4-[4-(4-Fluoro-3-trifluoromethyl-phenyl)-1H-imidazol-2-yl]-piperidine-1-carboxylic acid tert-butyl ester (18.23 g; 44.10 mmoles, 64.86% yield) as a white solid.

Add 4-[4-(4-Fluoro-3-trifluoromethyl-phenyl)-1H-imidazol-2-yl]-piperidine-1-carboxylic acid tert-butyl ester (16.03 g; 1.00 equiv; 38.77 mmoles) in 40 mL of dimethyl sulfoxide (DMSO) to a solution of potassium hydroxide (1.5 equiv; 58.16 mmoles; 3.26 g) in 200 mL of DMSO. After 5 min at RT, add methyl iodide (1.1 equiv; 42.65 mmoles; 2.66 mL) in one portion. Stir at RT for two hours, then pour the mixture into ice water. Filter the solid, wash with water, and dry under reduced pressure. Triturate the solid in hot heptane, filter and dried under reduced pressure to give 4-[4-(4-Fluoro-3-trifluoromethyl-phenyl)-1-methyl-1H-imidazol-2-yl]-piperidine-1-carboxylic acid tert-butyl ester (8.7 g; 52.49% yield) as a white solid.

Add hydrogen chloride (4.00 equiv; 81.41 mmoles; 20.35 mL) to a solution of 4-[4-(4-Fluoro-3-trifluoromethyl-phenyl)-1-methyl-1H-imidazol-2-yl]-piperidine-1-carboxylic acid tert-butyl ester (8.7 g; 1.00 equiv; 20.35 mmoles) in dichloromethane (101.77 mL), at RT. Stir the solution at RT for 1 hour. Remove the solvent under reduced pressure, and dissolve the crude in isopropyl alcohol (101.77 mL). Add 4-chloro-1H-pyrazolo[3,4-d]pyrimidine (1.65 equiv; 33.58 mmoles; 5.19 g) and triethylamine (10 equiv; 203.54 mmoles; 28.37 mL). Stir the mixture at reflux for 1 hour. Remove the solvent under reduced pressure and triturate the crude in water overnight. Filter the solid and triturate in hot acetonitrile, filter and dry in vacuo. 4-{4-[5-(4-Fluoro-3-trifluoromethyl-phenyl)-3-methyl-1H-imidazol-2-yl]-piperidin-1-yl}-1H-pyrazolo[3,4-d]pyrimidine (8.42 g; 18.86 mmoles; 92.66% yield) is obtained as a light yellow solid.

Add hydrogen chloride (1.1 equiv; 18.52 mmoles; 4.63 mL) to a suspension of 4-{4-[4-(4-fluoro-3-trifluoromethyl-phenyl)-1-methyl-1H-imidazol-2-yl]-piperidin-1-yl}-1H-pyrazolo[3,4-d]pyrimidine (7.5 g; 1.00 equiv; 16.84 mmoles) in dichloromethane (50 mL), and stir the mixture for 1 hour at RT. Remove the solvent in vacuo, and triturate the crude in MTBE for 1 hour. Filter the solid and dry in vacuo overnight to give 4-{4-[4-(4-Fluoro-3-trifluoromethyl-phenyl)-3-methyl-1H-imidazol-2-yl]-piperidin-1-yl}-1H-pyrazolo[3,4-d]pyrimidine hydrochloride (7.99 g; 16.58 mmoles; 98.47% yield) as a white solid. $^1$H-NMR (300 MHz, DMSO): δ14.01-13.99 (m, 1H), 8.57-8.54 (m, 2H), 8.26-8.19 (m, 3H), 7.72-

7.63 (m, 1H), 5.23-5.20 (m, 2H), 3.89 (s, 3H), 3.41 (m, 2H), 2.15-2.07 (m, 3H), 1.10 (s, 2H).

Preparation of 4-{4-[4-(4-Fluoro-3-trifluoromethyl-phenyl)-1-methyl-1H-imidazol-2-yl]-piperidin-1-yl}-1H-pyrazolo[3,4-d]pyrimidine p-toluenesulfonate Cool a solution of 4-fluoro-3-(trifluoromethyl)phenacyl bromide (93% pure by HPLC, 1000 g; 3.51 moles) and THF (5 L) to <5° C. in an ice bath. Add a solution of sodium azide (239 g; 3.68 moles, 1.05 eq) in water (800 mL) drop wise over one hour at <5° C. After stirring at <5° C. for one hour, separate and discard the aqueous layer. While still cold, add the organic layer slowly over 3 hours to a solution of triphenylphosphine (920.2 g, 3.51 moles, 1.0 eq), p-toluenesulfonic acid monohydrate (1335 g, 7.02 moles, 2.0 eq), and THF (5 L). Maintain the temperature at <15° C. throughout this addition and solids precipitate during the addition.

Stir the reaction mixture at <20° C. for 2 hours and then filter the solid, wash with THF (3×2 L), and dry at 50° C. under vacuum to give 1167.4 g (85%, 92% corrected for starting material purity) of 2-amino-1-(4-fluoro-3-trifluoromethyl-phenyl)-ethanone p-toluenesulfonate as a white crystalline solid.

Combine 2-amino-1-(4-fluoro-3-trifluoromethyl-phenyl)-ethanone p-toluenesulfonate (1133 g; 2.88 moles), 1-(tert-butoxycarbonyl)piperidine-4-carboxylic acid (795 g; 3.47 moles; 1.20 eq), THF (3450 mL), and ethyl acetate (7500 mL) to form a thin white slurry. Cool the slurry to <5° C. in ice bath and add 2-propanephosphonic acid anhydride ($T_3P$) (50% solution in EtOAc) (2385 g; 3.75 moles, 1.3 eq). Then add N-methylmorpholine (795 mL; 7.21 moles; 2.5 eq) over 1 hour, maintaining the temperature <10° C. Warm the resulting slurry to ambient temperature and stir for 2 hours.

Quench the reaction by addition of water. Separate the organic phase, then wash with aqueous $NaHCO_3$, aqueous NaCl. Warm the organic phase to 50° C. on a rotary evaporator and add n-heptane. Distill solvent under vacuum until the final slurry volume is approximately 5 L. Cool the slurry to RT and filter the solids, wash with n-heptane (2×1 L) and then dry in a vacuum oven at 50° C. overnight, resulting in 1-[2-(4-fluoro-3-trifluoromethyl-phenyl)-2-oxo-ethylcarbamoyl]-piperidine-4-carboxylic acid tert-butyl ester (1124.8 g, 90%) as a white solid.

Combine 1-[2-(4-fluoro-3-trifluoromethyl-phenyl)-2-oxo-ethylcarbamoyl]-piperidine-4-carboxylic acid tert-butyl ester (100 g, 231 mmoles), ammonium acetate (178.3 g; 2.31 moles; 10 eq), and methanol (1000 mL). The reactor used for this transformation is a coiled 1/16" I.D. stainless steel tube (total internal volume of tubing in oven is 541 mol). Heat the reactor in an oven to 140° C. Control the back pressure in this tube at 250 psig by a regulator to allow super-heating of the solution above its normal boiling point. Pump the solution prepared above continuously through the heated tube under pressure at 6.01 mL/min (affording a total residence time in the heated tube of 90 minutes). As the solution exits the oven, cool it back to 20° C. in a tube-in-tube heat exchanger. Once the entire solution process through the reactor (8 hours total processing time), concentrate the resulting orange solution under vacuum at 30° C. to a total volume of 600 mL. Add acetonitrile (200 mL) and heat the solution to 50° C. Add water (700 mL) drop wise with seeding over 2 hours to crystallize the product. Cool the resulting slurry to 20° C. and filter the solid, then wash with 20% MeOH in water (2×200 mL). Dry the resulting solid under vacuum at 50° C. Re-slurry the solid in acetonitrile (200 mL) at 50° C. Cool the slurry to ambient temperature, filter the solid and wash with acetonitrile (100 mL) to afford 4-[4-(4-fluoro-3-trifluoromethyl-phenyl)-1H-imidazol-2-yl]-piperidine-1-carboxylic acid tert-butyl ester (54.43 g; 132 mmoles; 57%) as an off white solid.

Dissolve 4-[4-(4-fluoro-3-trifluoromethyl-phenyl)-1H-imidazol-2-yl]-piperidine-1-carboxylic acid tert-butyl ester (80.02 g; 183.69 mmoles) in DMSO (1060 mL). Add KOH (18.47 g; 279.82 mmoles; 1.5 eq) in one portion. Add methyl iodide (27.74 g; 193.48 mmoles; 1.05 eq) over 30 minutes at 25° C. Stir the solution at 25° C. for 1 hour. Add a mixture of 4-[4-(4-fluoro-3-trifluoromethyl-phenyl)-1-methyl-1H-imidazol-2-yl]-piperidine-1-carboxylic acid tert-butyl ester seed crystals (0.17 g) and water (80 mL) over 5 minutes to the solution. Stir the resulting thin slurry at 25° C. for 30 minutes. Add additional water (240.73 mL) over 30 minutes at 25° C. Filter the solid and wash with 20% DMSO in water (2×120 mL) and then water (120 mL). Dry the solid under vacuum at 60° C. Dissolve the resulting dried solids in ethanol (480 mL) at 50° C. Add water (240 mL) over 5 minutes. Then add 4-[4-(4-fluoro-3-trifluoromethyl-phenyl)-1-methyl-1H-imidazol-2-yl]-piperidine-1-carboxylic acid tert-butyl ester seed (0.038 g) and more water (240 mL) over 30 minutes. Cool the resulting slurry to 25° C. over 2 hours. Filter the solids and wash the cake with 20% EtOH in water. Dry the solid under vacuum at 60° C. affording 4-[4-(4-fluoro-3-trifluoromethyl-phenyl)-1-methyl-1 H-imidazol-2-yl]-piperidine-1-carboxylic acid tert-butyl ester (72.36 g, 92%) as a white solid.

Prepare an anhydrous HCl solution by slow addition of acetyl chloride (193.14 mL; 2.71 moles; 4.00 eq) to methanol (1160 mL) over 45 minutes at <5° C. Add the resulting solution to a separate flask containing a solution of 4-[4-(4-fluoro-3-trifluoromethyl-phenyl)-1-methyl-1H-imidazol-2-yl]-piperidine-1-carboxylic acid tert-butyl ester (290 g; 678.46 mmoles) in methanol (2320 mL) over 90 minutes at 20° C. Stir the reaction mixture at 20° C. overnight. Concentrate the reaction mixture under vacuum at 30° C. Add DMSO (1080 mL; 15.20 moles; 1.08 L; 1.19 kg) and the distillation continues until the internal temperature reaches 50° C. at a pressure of 20 mm Hg. Add DMSO until the total volume is 2030 mL. Then add triethylamine (473 mL; 3.39 moles; 5 eq) via addition funnel over 30 minutes. Charge solid 4-chloro-1H-pyrazolo[3,4-d]pyrimidine (110.29 g; 713.58 mmoles; 1.05 eq) in equal portions equally spaced over 30 minutes. Stir the resulting slurry at 20° C. overnight. Heat the slurry to 80° C. Add water (229 mL) to afford a clear solution. Seed the reaction and add more water (1273 mL) slowly over 4 hours to fully crystallize the product. Cool the slurry to 50° C. and filter the solid. Wash the cake with 30% water in DMSO (2×290 mL), then water (290 mL). Dry the solids under vacuum at 60° C. to afford 4-{4-[4-(4-fluoro-3-trifluoromethyl-phenyl)-1-methyl-1H-imidazol-2-yl]-piperidin-1-yl}-1H-pyrazolo[3,4-d]pyrimidine (301 g, 99%) as an off white solid.

Dissolve 4-{4-[4-(4-fluoro-3-trifluoromethyl-phenyl)-1-methyl-1H-imidazol-2-yl]-piperidin-1-yl}-1H-pyrazolo[3,4-d]pyrimidine (20 g, 44.9 mmoles) in a 20:1 $H_2O$:acetone mixture (360 mL). Add a solution of p-toluenesulfonic acid monohydrate (10.25 g; 53.9 mmoles; 1.2 eq) in a 20:1 H$_2$O:acetone mixture (40 mL) to the reaction over 20 minutes at 20° C. Heat the reaction mixture to 55° C., hold for 1 hour, then cool to 25° C. over 1 hour. Filter the solid and wash the cake with water (40 mL). Drying under vacuum at 50° C. affords 4-{4-[4-(4-fluoro-3-trifluoromethyl-phenyl)-1-methyl-1H-imidazol-2-yl]-piperidin-1-yl}-1H-pyrazolo[3,4-d]pyrimidine p-toluenesulfonate (23.9 g; 86%) as a white solid.

Preparation of Crystalline 4-{4-[4-(4-Fluoro-3-trifluoromethyl-phenyl)-1-methyl-1H-imidazol-2-yl]-piperidin-1-yl}-1H-pyrazolo[3,4-d]pyrimidine p-toluenesulfonate To a 1-L round bottom flask with overhead stirrer charge with 60.12 g of 4-{4-[4-(4-Fluoro-3-trifluoromethyl-phenyl)-1-methyl-1H-imidazol-2-yl]-piperidin-1-yl}-1H-pyrazolo[3,4-d]pyrimidine (prepared according to either of the above preparations without the final salt formation step), followed by 250 mL of 5% aq. MeOH. Stir the resulting slurry and add p-toluenesulfonic acid monohydrate (26.88 g) followed by a rinse forward with the remaining 50 mL of 5% aq. MeOH. Stir the resulting slurry and cool the crystals to 5° C. After 1 h at 5° C., stop stirring and filter the slurry on a Buchner funnel Rinse the flask out with 75 mL of cold 5% aq. MeOH and use this rinse to wash the filter cake. Transfer the solids to a weighing dish and dry at 50° C. in vacuo all day and all night, with a slow air bleed. The final weight is 71.44 g.

X-ray powder diffraction analysis is performed with a D4 Endeaver diffractometer, equipped with a CuKa source ($\lambda$=1.54056 Å) operating at 40 kV and 50 mA. The sample is scanned from 4° to 40° in 2θ, with a step size of 0.009 in 2θ and a scan rate of ≧1.5 sec per step.

| Angle 2-theta (±0.1°) | Intensity % |
|---|---|
| 6.826 | 12 |
| 10.256 | 24 |
| 12.984 | 24 |
| 13.131 | 61 |
| 13.431 | 25 |
| 13.688 | 100 |
| 14.062 | 24 |
| 15.745 | 6 |
| 17.121 | 15 |
| 18.599 | 5 |
| 18.919 | 21 |
| 19.38 | 29 |
| 20.603 | 14 |
| 21.661 | 6 |
| 21.962 | 14 |
| 22.108 | 9 |
| 23.485 | 14 |
| 23.615 | 17 |
| 23.866 | 22 |
| 24.024 | 20 |
| 24.667 | 11 |
| 24.795 | 11 |
| 25.029 | 8 |
| 25.552 | 9 |
| 26.234 | 5 |
| 26.556 | 10 |
| 27.031 | 6 |

-continued

| Angle 2-theta (±0.1°) | Intensity % |
|---|---|
| 27.693 | 11 |
| 27.97 | 5 |
| 28.352 | 6 |
| 28.428 | 5 |
| 38.232 | 5 |

Determination of In Vivo Efficacy

A549 human non-small-cell lung carcinoma cells (5×10$^6$) are subcutaneously implanted into the flank of female C.B-17 (Fox Chase SCID) Model #CB17SC-M mice in 0.2 mL of matrigel. Approximately 1 week post-implantation when the tumor size is approximately 100 mg, mice are randomized into groups of 10 and dosed orally once daily at 2.5 mg/kg 4-[4-[4-(4-fluoro-3-trifluoromethyl-phenyl)-1-methyl-1H-imidazol-2-yl]-piperidin-1-yl]-1H-pyrazolo[3,4-d]pyrimidine (the p70 S6 kinase inhibitor; formulated in 35% PEG300/10% HPBCD/10% PS80 in H$_2$O; concentration of inhibitor is 0.31 mg/mL) or 20 mg/kg erlotinib hydrochloride (formulated in NaCMC Tween 80; concentration of erlotinib hydrochloride is 2.5 mg/mL) or in combination (2.5 mg/kg of the p70 S6 kinase inhibitor and 20 mg/kg of erlotinib hydrochloride). The vehicle group is given the 2 vehicles (NaCMC Tween 80 and 35% PEG300/10% HPBCD/10% PS80 in H$_2$O) in combination (0.1 mL of each). Treatment is continued for 38 days. Tumor volumes are measured using standard technique twice weekly and reported. Tumor size and body weight are recorded and analyzed bi-weekly. Tumor volume is estimated by using the formula: v=l×w$^2$×0.536 where l=larger of measured diameter and w=smaller of perpendicular diameter. The analysis uses SAS software version 8.2 (SAS Institutes Inc, Cary, N.C.) to analyze the log tumor volume data using a repeated measures ANOVA model with a spatial power covariance structure. For each time point taken, treatment groups are compared to the vehicle control group. Tumor volumes are given as means±standard errors for each treatment group determined from a repeated measures ANOVA on each group. (SAS for Mixed Models, 2$^{nd}$ Ed., Littell et al., 2006, SAS Institutes Inc, Cary, N.C.).

Statistical Analysis of Compound Interaction

The tumor volume vs. time data for each animal is used to calculate an area under the curve (AUC) using the trapezoid rule. These AUCs are analyzed by 2-way ANOVA using a log transformation to equalize variance across groups. The two factors are the dose of 4-[4-[4-(4-fluoro-3-trifluoromethyl-phenyl)-1-methyl-1H-imidazol-2-yl]-piperidin-1-yl]-1H-pyrazolo[3,4-d]pyrimidine and the dose of erlotinib hydrochloride. The interaction effect between the factors is used to test for departure from additivity. (An Introduction to Statistical Methods and Data Analysis, R. Lyman Ott, 1993, Duxbury Press, Belmont, Calif.)

The results of this study are shown in the table below. n (the number of mice) is 9 for all the data, except for the data from day 17 onwards in the vehicle group and the data from day 38 onwards in the erlotinib hydrochloride group when it is 8. The data in the column headed Signif. indicates whether the difference relative to the vehicle group is statistically significant: NS=Not Significant ($p>0.05$); *=$0.01<p\leq0.05$; =$0.001<p\leq0.01$; *=$p\leq0.001$.

|  | Vehicle | | p70 S6 Kinase Inhibitor Only | | | Erlotinib Hydrochloride Only | | | P70 S6 Kinase Inhibitor and Erlotinib Hydrochloride in Combination | | |
|---|---|---|---|---|---|---|---|---|---|---|---|
| Day | Mean | SE | Mean | SE | Signif. | Mean | SE | Signif. | Mean | SE | Signif. |
| 7 | 40.3 | 4.5 | 33.8 | 4.8 | NS | 39.5 | 3.6 | NS | 35.8 | 5.9 | NS |
| 9 | 52.7 | 5.1 | 51.9 | 6.2 | NS | 51.5 | 4.7 | NS | 52.6 | 6.6 | NS |
| 14 | 67.7 | 6.7 | 56.2 | 6.5 | NS | 61.8 | 7.6 | NS | 48.3 | 7.5 | NS |
| 17 | 86.6 | 10.2 | 75.9 | 11 | NS | 74.8 | 11.1 | NS | 54.4 | 6.5 | * |
| 21 | 110.1 | 16.9 | 94.1 | 15.2 | NS | 91.1 | 13.4 | NS | 75.1 | 10.6 | NS |
| 24 | 139.3 | 18.9 | 113.5 | 23.2 | NS | 101.6 | 13.9 | NS | 74.2 | 8.6 | ** |
| 28 | 208.2 | 22.9 | 196.6 | 22.6 | NS | 139.9 | 21.7 | NS | 89.8 | 9.9 | *** |
| 31 | 279.1 | 27.2 | 231.3 | 24.9 | NS | 141.8 | 17.4 | ** | 118.4 | 13 | *** |
| 35 | 347.6 | 38.2 | 302.4 | 41 | NS | 196.7 | 29.3 | ** | 127.6 | 14 | *** |
| 38 | 426.2 | 47.5 | 353.3 | 46.1 | NS | 259.4 | 35.9 | * | 157 | 24.6 | *** |
| 42 | 500 | 64.8 | 425.5 | 66.2 | NS | 260.1 | 42.1 | ** | 198.3 | 27.8 | *** |
| 44 | 576.2 | 74.3 | 530.9 | 71 | NS | 373.8 | 39.7 | * | 253.7 | 34.2 | *** |

The log tumor volume AUC for the combination (3.58) is statistically different (p<0.0008) from the vehicle (3.91), whereas the log tumor volume AUC values for the p70 S6 kinase inhibitor only (3.85) and erlotinib hydrochloride only (3.76) treatment groups are not significantly different from the vehicle. The p70 S6 kinase inhibitor only and erlotinib hydrochloride only treatment groups are also significantly different from the combination group in pairwise comparisons of the log tumor volume AUC values.

When combined with the EGFR inhibitor erlotinib hydrochloride, 4-[4-[4-(4-fluoro-3-trifluoromethyl-phenyl)-1-methyl-1H-imidazol-2-yl]-piperidin-1-yl]-1H-pyrazolo[3,4-d]pyrimidine shows the ability to inhibit the growth of A549 non-small-cell lung cancer tumors. In this study 4-[4-[4-(4-fluoro-3-trifluoromethyl-phenyl)-1-methyl-1H-imidazol-2-yl]-piperidin-1-yl]-1H-pyrazolo[3,4-d]pyrimidine was dosed at 2.5 mg/kg QD ×35 and erlotinib hydrochloride at 20 mg/kg QD ×35. These doses were sub-optimal doses for each agent and the combination showed enhanced efficacy compared to the p70 S6 kinase inhibitor only and erlotinib hydrochloride only groups. The combination treatment did not result in any overt toxicity.

These results show that modulating the PI3K pathway upstream and downstream will result in greater efficacy.

I claim:

1. A method of treating a cancer selected from the group consisting of non-small-cell lung cancer, small-cell lung cancer, and cisplatin-resistant small-cell lung cancer comprising administering to a patient in need thereof a compound 4-[4-[4-(4-fluoro-3-trifluoromethyl-phenyl)-1-methyl-1H-imidazol-2-yl]-piperidin-1-yl]-1H-pyrazolo[3,4-d]pyrimidine, or a pharmaceutically acceptable salt thereof, and an EGFR inhibitor in amounts that in combination are effective.

2. The method according to claim 1 wherein the EGFR inhibitor is erlotinib hydrochloride.

3. The method according to claim 1 wherein the compound 4-[4-[4-(4-fluoro-3-trifluoromethyl-phenyl)-1-methyl-1H-imidazol-2-yl]-piperidin-1-yl]-1H-pyrazolo[3,4-d]pyrimidine, or a pharmaceutically acceptable salt thereof, is 4-[4-[4-(4-fluoro-3-trifluoromethyl-phenyl)-1-methyl-1H-imidazol-2-yl]-piperidin-1-yl]-1H-pyrazolo[3,4-d]pyrimidine tosylate.

4. The method according to claim 1 wherein the compound 4-[4-[4-(4-fluoro-3-trifluoromethyl-phenyl)-1-methyl-1H-imidazol-2-yl]-piperidin-1-yl]-1H-pyrazolo[3,4-d]pyrimidine, or a pharmaceutically acceptable salt thereof, and the EGFR inhibitor are administered orally.

5. A pharmaceutical composition comprising a compound 4-[4-[4-(4-fluoro-3-trifluoromethyl-phenyl)-1-methyl-1H-imidazol-2-yl]-piperidin-1-yl]-1H-pyrazolo[3,4-d]pyrimidine, or a pharmaceutically acceptable salt thereof, and an EGFR inhibitor.

6. The pharmaceutical composition of claim 5 wherein the EGFR inhibitor is erlotinib hydrochloride.

* * * * *